US007224162B2

(12) United States Patent
Proett et al.

(10) Patent No.: US 7,224,162 B2
(45) Date of Patent: May 29, 2007

(54) SYSTEM AND METHODS FOR UPSCALING PETROPHYSICAL DATA

(75) Inventors: Mark A. Proett, Missouri City, TX (US); James M. Fogal, Houston, TX (US); Wilson C. Chin, Houston, TX (US); Prabhakar R. Aadireddy, Cypress, TX (US)

(73) Assignee: Halliburton Energy Services Group, Inc., Houston, TX (US)

( * ) Notice: Subject to any disclaimer, the term of this patent is extended or adjusted under 35 U.S.C. 154(b) by 0 days.

(21) Appl. No.: 10/957,402

(22) Filed: Oct. 1, 2004

(65) Prior Publication Data
US 2005/0116709 A1 Jun. 2, 2005

(51) Int. Cl.
*G01V 3/00* (2006.01)

(52) U.S. Cl. .......................................... 324/303; 702/6

(58) Field of Classification Search ................ 324/303, 324/300; 702/6
See application file for complete search history.

(56) References Cited

U.S. PATENT DOCUMENTS

| 4,625,547 | A | * | 12/1986 | Lyle, Jr. ................... 73/152.05 |
| 4,710,713 | A | | 12/1987 | Strikman |
| 4,717,876 | A | | 1/1988 | Masi et al. |
| 4,717,877 | A | | 1/1988 | Taicher et al. |
| 4,717,878 | A | | 1/1988 | Taicher et al. |
| 4,742,459 | A | * | 5/1988 | Lasseter ...................... 702/12 |
| 4,890,487 | A | | 1/1990 | Dussan V. et al. |
| 4,939,648 | A | | 7/1990 | O'Neill et al. |
| 5,055,787 | A | | 10/1991 | Kleinberg et al. |
| 5,055,788 | A | | 10/1991 | Kleinberg et al. |
| 5,212,447 | A | | 5/1993 | Paltiel |
| 5,265,015 | A | | 11/1993 | Auzerais et al. |
| 5,269,180 | A | | 12/1993 | Dave et al. |
| 5,279,153 | A | | 1/1994 | Dussan V. et al. |
| 5,280,243 | A | | 1/1994 | Miller |
| 5,299,128 | A | * | 3/1994 | Antoine et al. ................ 702/10 |
| 5,309,098 | A | | 5/1994 | Coates et al. |
| 5,329,448 | A | * | 7/1994 | Rosthal ......................... 702/7 |
| 5,412,320 | A | | 5/1995 | Coates |
| 5,417,104 | A | * | 5/1995 | Wong ............................ 73/38 |
| 5,517,115 | A | | 5/1996 | Prammer |
| 5,557,200 | A | | 9/1996 | Coates |
| 5,602,334 | A | | 2/1997 | Proett et al. |
| 5,644,076 | A | | 7/1997 | Proett et al. |

(Continued)

OTHER PUBLICATIONS

J. David. Moulton, Stephan Knapek, and Joel E. Dendy. Multilevel upscaling in heterogeneous porous media. Research Highlights LA-UR 99-4754, Center for Nonlinear Studies, Los Alamos National Laboratory, Los Alamos, NM, Jan. 1999.*

(Continued)

*Primary Examiner*—Louis M. Arana
(74) *Attorney, Agent, or Firm*—Jones Day

(57) ABSTRACT

System and methods for estimating properties of a geologic formation are disclosed. A preferred embodiment includes a method for estimating properties of a geologic formation, comprising the steps of: measuring a property of the formation in two or more directions along a path in the formation; obtaining directional property values for at least one spatial unit along the path in the formation based on the property measurements; and providing an anisotropy estimate of the formation from the obtained directional property values.

46 Claims, 11 Drawing Sheets

U.S. PATENT DOCUMENTS

| | | | |
|---|---|---|---|
| 5,672,819 A | | 9/1997 | Chin et al. |
| 5,675,147 A | * | 10/1997 | Ekstrom et al. ............ 250/256 |
| 5,696,448 A | | 12/1997 | Coates et al. |
| 5,757,191 A | * | 5/1998 | Gianzero .................... 324/339 |
| 5,936,405 A | | 8/1999 | Prammer et al. |
| 6,005,389 A | | 12/1999 | Prammer |
| 6,023,164 A | | 2/2000 | Prammer |
| 6,051,973 A | | 4/2000 | Prammer |
| 6,107,796 A | | 8/2000 | Prammer |
| 6,111,408 A | * | 8/2000 | Blades et al. ............... 324/303 |
| 6,242,913 B1 | | 6/2001 | Prammer |
| 6,255,819 B1 | | 7/2001 | Day et al. |
| 6,268,726 B1 | | 7/2001 | Prammer et al. |
| 6,327,538 B1 | | 12/2001 | Chin |
| 6,362,619 B2 | | 3/2002 | Prammer et al. |
| 6,512,371 B2 | | 1/2003 | Prammer |
| 6,525,534 B2 | | 2/2003 | Akkurt et al. |
| 6,531,868 B2 | | 3/2003 | Prammer |
| 6,541,969 B2 | | 4/2003 | Sigal et al. |
| 6,577,125 B2 | | 6/2003 | Prammer et al. |
| 6,583,621 B2 | | 6/2003 | Prammer et al. |
| 6,987,385 B2 | | 1/2006 | Akkurt et al. |
| 2003/0094040 A1 | | 5/2003 | Proett et al. |

OTHER PUBLICATIONS

The Mathworks, Inc., Image Processing Toolbox For Use with MATLAB, User's Guide, Version 2, May 1997.*

Ayan C et al., "Measuring Permeability Anisotropy: The Latest Approach", Oilfield Review vol. 6, No. 4, pp. 24-35. Oct. 1994.*

Xian H-W et al., "Upscaling Hydraulic Conductivities in Heterogenous Media: An Overview", Journal of Hydrology 183, pp. ix-xxxii, 1996.*

Burley et al., IUN/FYDE Introductory Physics Notes, http://theory.uwinnipeg.ca/physics/index.html , Feb. 5, 1996; specifically . . . /physics/curr/node3.html , . . . /node6.html , and . . . /node7.html.*

Davidson, L et al., Soil Mechanics, http://fbe.uwe.ac.uk/public/geocal/SoilMech/water/water.htm , May 2000.*

Wen XH and Gomez-Hernandez JJ, "Upscaling hydraulic conductivities in heterogeneous media: an overview", J Hydrology 183 (1996) pp. ix-xxxii.*

Lindsay R and van Koughnet R, "Sequential Backus Averaging: Upscaling well logs to seismic wavelengths", The Leading Edge, vol. 20, Issue 2, pp. 188-191 (Feb. 2001).*

Ezzedine S and Rubin Y, "Bayesian integration of hydrogeological and geophysical data for site characterization: theory and application to the LLNL superfund site", Berkeley Symposium entitled "Bridging the Gap Between Measurements and Modeling in Heterogeneous Media", Berkeley CA, Mar. 25-28, 2002.*

Chandler et al., "Improved log quality with a dual-frequency pulsed NMR tool," SPE 28365, 69th Ann. Tech. Conf. of the SPE, Sep. 25-28, 1994, 23-35.

Delhomme et al., "Permeability and Porosity Upscaling in the Near-Wellbore Domain: The Contribution of Borehole Electrical Images", SPE 36822, Europ. Petrol. Conf. Oct. 22-24, 1996,89-101.

Georgi et al., "On the Relationship between Resistivity and Permeability Anisotropy", SPE 77715, 77th Ann. Techn. Conf. of the SPE, Sep. 29-Oct. 2, 2002 (14 pages).

International Search Report of PCT US2004/032335 (WO 2005/036338) mailed on Dec. 28, 2005.

Joshi, Horizontal Well Technology, Pennwell Publishing Company, 1991.

Kleinberg et al., "Novel NMR apparatus for investigating an external sample," J. Magnetic Resonance, 1992, 97:466-485.

McKeon et al., "An improved NMR tool design for faster logging," SPWLA 40th Ann. Logging Symp., May 30-Jun. 3, 1999 (14 pages).

Mesri et al., "Mechanisms controlling the permeability of clays," Clays and Clay Minerals, 1971, 19:151-158.

Miller et al., "Spin echo magnetic resonance logging: Porosity and free fluid index determination," SPE 20561, 65th Ann. Tech. Conf., Sep. 23-26, 1990.

Nelson, "Permeability-porosity relationships in sedimentary rocks," The Log Analyst, May-Jun. 1994, 38-62.

Revil et al., "Permeability of shaly sands," Water Resources Research, Mar. 1999, 35(3): 651-662.

Tabanou et al., "Thinly laminated reservoir evaluation in oil-base mud: High resolution versus bulk anisotropy measurement—a comprehensive evaluation," SPWLA 43rd Ann. Logging Symp. (14 pages).

Van Baaren, "Quick-look permeability estimates using sidewall samples and porosity logs," 6th Ann. European Logging Symp. Transactions, SPWLA, 1979.

Vernik, "Permeability Prediction in Poorly Consolidated Siliciclastics Based on Porosity and Clay Volume Logs," Petrophysics, Mar.-Apr. 2000, 138-147.

Witt et al., A comparison of wireline and drillstern test fluid samples from a deepwater gas-condensate exploration well, SPE 56714, 1999 SPE Ann. Tech. Conf. and Exhibit., Oct. 3-6, 1999, 515-524.

Wu et al., "Inversion of multi-phase petrophysical properties using pumpout sampling data acquired with a wireline formation tester," SPE 77345, 2002 (16 pages).

PCT Written Opinion for International Application No. PCT/US04/32335 mailed on Dec. 28, 2005.

* cited by examiner kv/kh_av – running average
kv/kh – based on zoned criterion.

SYSTEM AND METHODS FOR UPSCALING PETROPHYSICAL DATA

FIELD OF THE INVENTION

The present invention relates generally to petrophysical data processing and in particular to a system and methods for generating directional formation property values based on measurement data obtained at different locations along a measurement path.

BACKGROUND OF THE INVENTION

In oil and gas exploration it is desirable to understand the structure and properties of the geological formation surrounding a borehole in order to determine if the formation contains hydrocarbon resources (oil and/or gas), to estimate the amount and producibility of hydrocarbon contained in the formation, and to evaluate the best options for completing the well in production. A significant aid in this evaluation is the use of wireline logging and/or logging-while-drilling (LWD) or measurement-while-drilling (MWD) measurements of the formation surrounding the borehole (referred to collectively as "logs" or "log measurements"). Typically, one or more logging tools are lowered into the borehole and the tool readings or measurement logs are recorded as the tools traverse the borehole. These measurement logs are used to estimate the desired formation properties.

One popular way to obtain the measurement logs is NMR logging. NMR logging has become very important for purposes of formation evaluation and is one of the preferred methods for determining formation parameters because of its non-destructive character. Improvements in the NMR logging tools, as well as advances in data analysis and interpretation allow log analysts to generate detailed reservoir description reports, including clay-bound and capillary-bound related porosity, estimates of the amounts of bound and free fluids, fluid types (i.e., oil, gas and water), permeability and other properties of interest. In general, NMR logging devices may be separate from the drilling apparatus (in what is known as wireline logging), or they may be lowered into the borehole along with the drilling apparatus, enabling NMR measurement while drilling is taking place. The latter types of tools are known in the art as logging-while-drilling (LWD) or measurement-while-drilling (MWD) logging tools.

NMR tools used in practical applications include, for example, the centralized MRIL® tools made by NUMAR Corporation, a Halliburton company, and the sidewall CMR tool made by Schlumberger. The MRIL® tool is described, for example, in U.S. Pat. No. 4,710,713 and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23-26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25-28, 1994. Certain details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115; 5,557,200; 5,696,448; 5,936,405; 6,005,389; 6,023,164; 6,051,973; 6,107,796; 6,111,408; 6,242,913; 6,255,819; 6,268,726; 6,362,619; 6,512,371; 6,525,534; 6,531,868; 6,541,969; 6,577,125 and 6,583,621, as well as in application Ser. No. 60/474,747, filed on May 3, 2003, to the same assignee as the present application. The structure and operation of the Schlumberger CMR tool is described, for example, in U.S. Pat. Nos. 4,939,648; 5,055,787 and 5,055,788 and further in "Novel NMR Apparatus for Investigating an External Sample," by Kleinberg, Sezginer and Griffin, J. Magn. Reson. 97, 466–485, 1992; and "An Improved NMR Tool Design for Faster Logging," D. McKeon et al., SPWLA 40$^{th}$ Annual Logging Symposium, May-June 1999. The contents of the above patents and patent applications are hereby expressly incorporated by reference for all purposes, and all non-patent references are incorporated by reference for background.

An application of NMR and other logging techniques is using measurement data to analyze the anisotropy of certain properties of the geological formation. Such properties may include permeability, porosity, resistivity, diffusivity, or viscosity. Anisotropic analysis of properties is particularly useful in reservoir engineering in which data or logs obtained through multiple measurements at different locations need to be combined, so that each flow interval of the geological area is characterized by a single anisotropy, such as permeability anisotropy. The process of combining data is often referred to as "up-scaling". Up-scaling can be very difficult because the measurement data are often taken at various scales and using different sample sizes. Moreover, without a well-defined algorithm to combine the data, an upscaled log is difficult to create for a path comprising a plurality of possibly different spatial units.

One purpose of upscaling is to use the single anisotropy, such as permeability anisotropy obtained for a flow interval, to predict the producibility of a well. Such performance prediction is traditionally made following well testing. However, the petrophysical industry is becoming more and more reluctant to perform well testing due to the increasing economical and environmental costs. Research is under way to determine whether alternatives, such as wireline formation tests, can be used to replace well test. (See, e.g., "A Comparison of Wireline and Drillstem Test Fluid Samples from a Deep Water Gas-Condensate Exploration Well", by Witt et al., paper 56714 presented at the 1999 SPE Annual Technical Conference and Exhibition, Houston, Tex., Oct. 3-6, 1999, the content of which are hereby expressly incorporated by reference for additional background.) Developing methods and systems for efficiently creating upscaled logs based on measurement data obtained along a path (or paths) in wireline formation tests can therefore stimulate the transition from well testing to wireline formation tests.

There is therefore a need to develop upscaling method(s), preferably capable of combining different types of data, including core data, wireline logs, wireline tester data and well testing. There is also a need to develop a system to implement the up-scaling method(s).

SUMMARY OF THE INVENTION

In one aspect, the present invention provides a method for investigating a geologic formation, comprising the steps of: measuring a property of the formation in one or more directions along a path in the formation; associating directional property value(s) with a plurality of spatial units along the path in the formation based on the property measurements; and providing a directional property log for the path in the formation, the log being upscaled from the directional property values associated with the plurality of spatial units.

The present invention further includes a system for investigating a geologic formation, including in a preferred embodiment an NMR logging device, a formation tester, such as the RDT tool made by Halliburton Corporation and others. The system also comprises one or more software programs adapted to execute data upscaling as described herein.

BRIEF DESCRIPTION OF THE DRAWINGS

Other objects and many attendant features of this invention will be appreciated and better understood with reference to the following detailed description when considered in connection with the accompanying drawings, wherein.

DETAILED DESCRIPTION OF THE INVENTION

Figure 1:
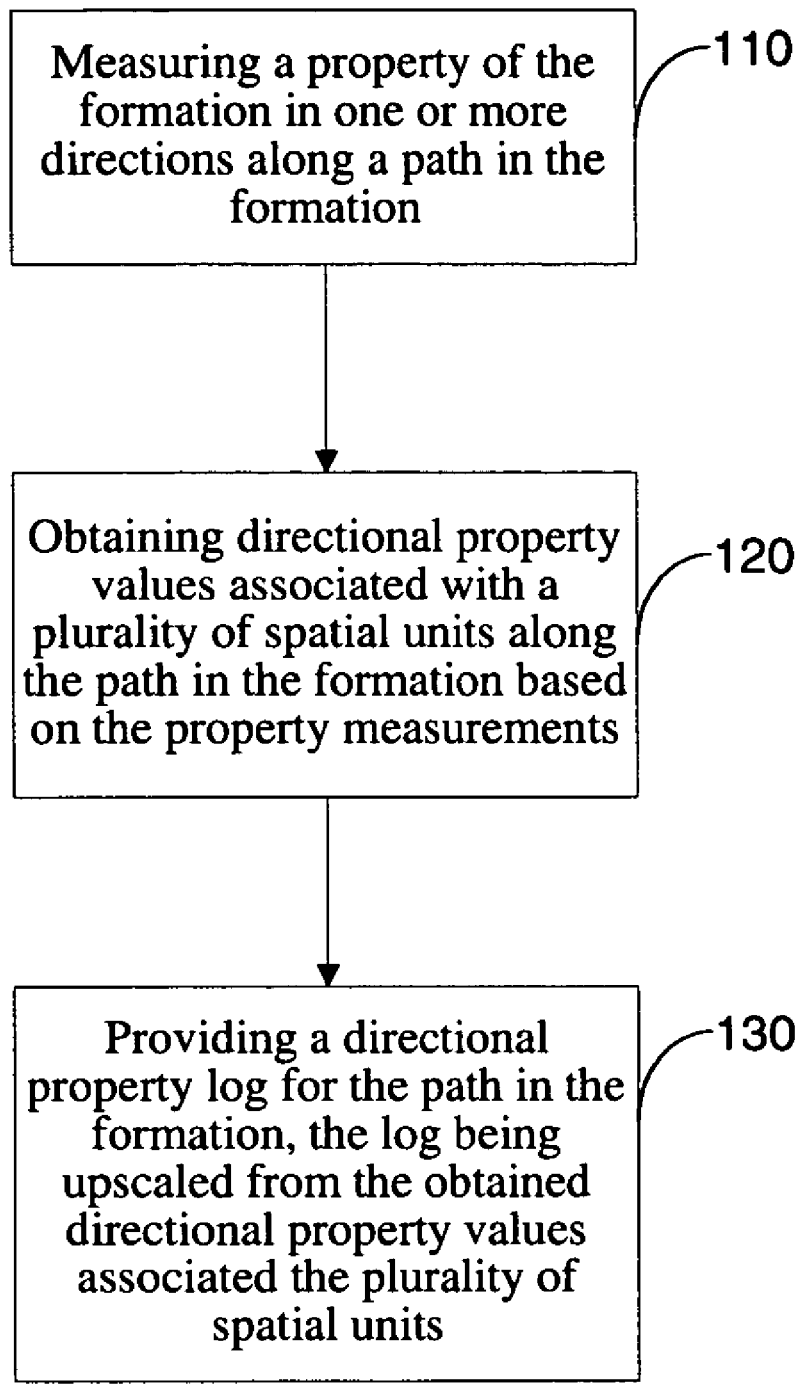
FIG. 1 is a flow chart of an upscaling method in one embodiment of the present invention.

In one aspect, the present invention is directed to methods for upscaling data in the investigation of a geologic formation. A flow chart illustrating the generalized method is shown in FIG. 1. In step 110, measurements of a property of the formation are obtained in one or more preferably orthogonal directions (usually horizontal or vertical), along a path in the formation. This path may be provided by a borehole drilled in the formation or, in a specific embodiment, may be generated in the process of drilling a borehole.

It is desirable that the type of property being measured or estimated is useful in the petrophysical examination of the formation and may be anisotropic in nature. Examples of properties that can be used include, without limitation, permeability, resistivity, porosity, diffusivity and viscosity. In a preferred embodiment of the invention discussed for illustration purposes below, the property being determined is the formation permeability.

In accordance with the present invention, measurements associated with the desired property can be made using any suitable device. In a specific embodiment, such measurements can be obtained, for example, by using NMR logging tools, such as the MRIL® tools by Halliburton Corp., the CMR-series tools by Schlumberger, or others. Other types of measurements can also be obtained using formation testers, such as the reservoir description tool (RDT) by Halliburton Corp., the modular formation dynamics tester (MDT) tool by Schlumberger, the Reservoir Characterization Instrument (RCI) by Baker Atlas, and others. Additionally similar measurements taken with core sample can be utilized since they are also typically distributed along the well bore thus containing directional information.

The measurements may be taken at a plurality of locations along a path in the formation traversed by a borehole. In one embodiment, the measurements are taken using a testing device (such as described in the preceding paragraph) at a plurality of depth points along a linear or other type of path, as permitted by the specifications of the device. As noted, the measurement data obtained may be any data related to the property estimation, and may include core data, wireline logs, wireline tester data, formation pressure measurements, well testing data, as well as 2D or 3D borehole electrical image data.

In step 120 of the method, directional property values, such as horizontal or vertical permeability values, are associating with a plurality of spatial units along the path in the formation based on the property measurement data obtained in step 110. Methods and systems for obtaining directional permeability values based on various property measurements are discussed, for example, in U.S. Pat. Nos. 5,672,819; 5,644,076; 5,602,334; 4,742,459; 5,269,180; 4,890,487; 5,279,153; 5,265,015 and 6,327,538, as well as in U.S. patent application Ser. No. 10/254,310, filed on Sep. 25, 2002, to the same assignee as the present application. The above references are hereby expressly incorporated by reference.

Directional values of other properties, such as resistivity or porosity can also be obtained using methods and systems known in the art. For example, methods and systems for determining directional resistivity values are discussed in "Thinly Laminated Reservoir Evaluation in Oil-Based Mud: High Resolution versus Bulk Anisotropy Measurement—A Comprehensive Evaluation", by Tabanou, et al., SPWLA, 43$^{rd}$ Annual Logging Symposium, Jun. 2–5, 2002, the contents of which are incorporated herein by reference for additional background. Porosity measurements are made available by NMR logging devices and are described in the reference listed in the background portion of the disclosure.

Permeability analysis, which is used in a preferred embodiment of the invention, is important because permeability anisotropy determination is key to efficient hydrocarbon exploitation. For example, when drilling vertical or near vertical wells, the ratio of the vertical to horizontal permeability is used in coning calculations and in reservoir simulation history matching to control the rate at which secondary gas caps appear. Moreover, when drilling horizontal, near horizontal, or vertical wells, knowing the permeability anisotropy provides crucial information needed to plan the optimum wellbore trajectory. For example, when a reservoir is relatively homogeneous, the ratio of the vertical to horizontal permeability is close to unity, it is then very beneficial to drill horizontal wells. (For details, see Horizontal Well Technology, by Joshi, Pennwell Publishing Company, Tulsa, Okla., 1991.) When the reservoir is laminate and the above permeability ratio is small, the preference is to drill vertical or near vertical wells. Associating directional permeability values with different spatial units is discussed below.

After associating directional property values with spatial units, a directional property log may be provided for the path in the formation in step 130 of the method. In one embodiment, the directional property log is provided in a format recognizable by a human, such as a graph. The log may contain property estimates upscaled from the obtained directional property values associated with the plurality of spatial units. In one embodiment of the present invention, directional permeability values at different depth points in a flow interval are upscaled to provide a single horizontal or vertical permeability estimate for each flow interval.

To upscale the horizontal permeability, in one embodiment it can be assumed that the fluid flow is completely horizontal and flows radially into the wellbore. With this assumption the equivalent horizontal permeability scales much the same as a network of parallel resistors over the depth interval where the resistance to flow is $1/(\Delta h\ k_{hi})$. Specifically, to upscale horizontal permeability, first recall that permeability is defined according to Darcy's law as follows:

$$\frac{dp}{dx} = \frac{\mu}{k} v \qquad (1)$$

where k is permeability, dp is the differential pressure, dx is the differential length, $\mu$ is viscosity, and v is fluid velocity. Assuming linear Darcy flow, the following simpler linear equation can be used:

$$\Delta P = h \frac{\mu}{k} \frac{Q}{A} \qquad (2)$$

where $\Delta P$ is the differential pressure across section; h is the length of section; Q is the flow rate; and A is the area of the section.

When producing reservoir fluids into a wellbore it is useful to resolve Darcy's law into radial coordinates where the flow rate is related to the pressure gradient into the reservoir as follows:

$$\Delta P = \frac{Q}{kh} \frac{\mu}{2\pi} \ln\left[\frac{r}{r_w}\right] \qquad (3)$$

Figure 2:
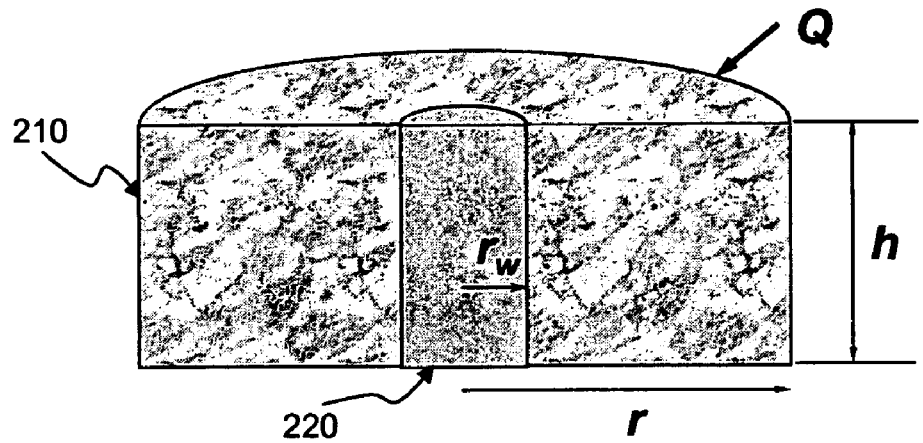
FIGS. 2–4 illustrate variables used to derive anisotropy data in different embodiments of the present invention.

The relationships between $\Delta P$, $r_w$, r, h, and Q are illustrated in FIG. 2. In FIG. 2, r is the radius into reservoir 210, $r_w$ is the radius of wellbore 220. $\Delta P$ is the differential pressure across $r_w$-r, h is the length of the reservoir 210, and Q is the flow rate of reservoir 210.

Figure 3:
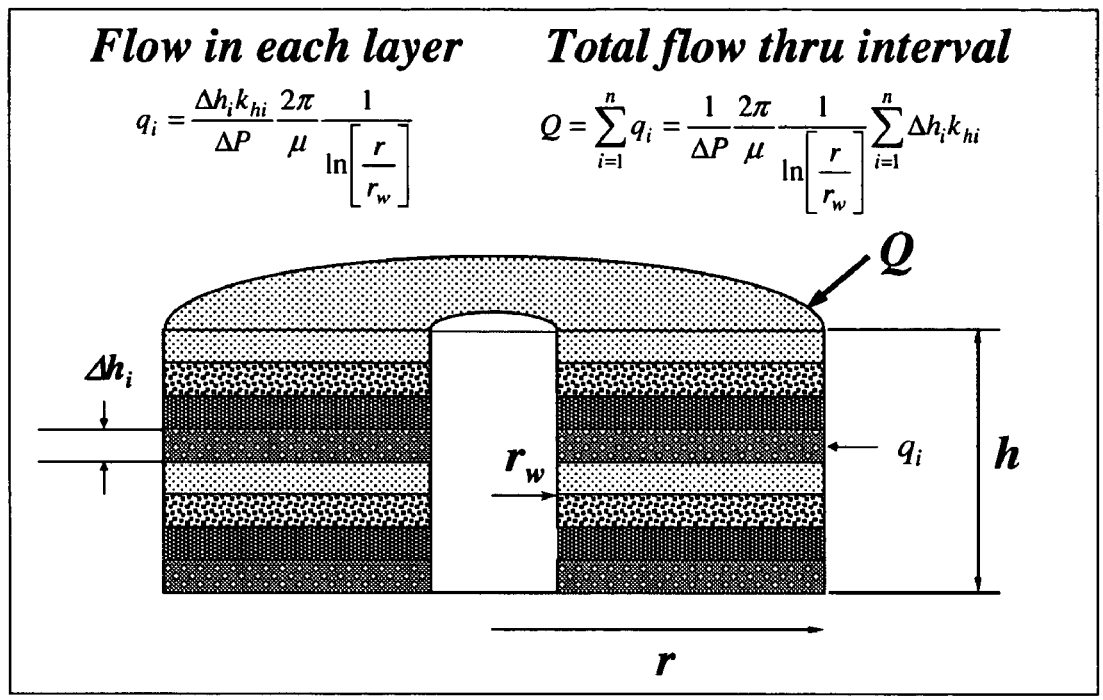

Assuming that a flow interval of the reservoir 210 is a layered structure as illustrated in FIG. 3, let n be the number of layers or depth points, i be a sequential layer number, $\Delta h_i$ be the height of layer i, $q_i$ be the flow rate through layer i, $k_{hi}$ be the horizontal permeability of layer i and $k_{he}$ be the interval's equivalent horizontal permeability fluid flow in a parallel through the layers. In this disclosure, a layer need not correspond to a physical layer of the formation, but may also be associated with units in the vertical resolution of the testing device. The flow rate $q_i$ through a layer i can be determined using Eq. 4:

$$q_i = \frac{\Delta h_i k_{hi}}{\Delta P} \frac{2\pi}{\mu} \frac{1}{\ln\left[\frac{r}{r_w}\right]} \qquad (4)$$

These flow rates are summed and then the total flow rate is equated to an equivalent horizontal permeability over the interval:

$$Q = \frac{\Delta h k_{he}}{\Delta P} \frac{2\pi}{\mu} \frac{1}{\ln\left[\frac{r}{r_w}\right]} \sum_{i=1}^{n} q_i = \frac{1}{\Delta P} \frac{2\pi}{\mu} \frac{1}{\ln\left[\frac{r}{r_w}\right]} \sum_{i=1}^{n} \Delta h_i k_{hi} \qquad (5)$$

This equation can be reduced and the equivalent horizontal permeability $k_{he}$ of the spatial interval (or generalized unit) can be determined as:

$$k_{he} = \frac{1}{h} \sum_{i=1}^{n} \Delta h_i k_{hi} \qquad (6)$$

If all the layers have a uniform thickness $\Delta h$, as would be the case with NMR logs, then a further simplification to Eq. 6 can be made.

$$k_{he} = \frac{\Delta h}{h} \sum_{i=1}^{n} k_{hi} = \frac{1}{n} \sum_{i=1}^{n} k_{hi} \qquad (7)$$

Figure 4:
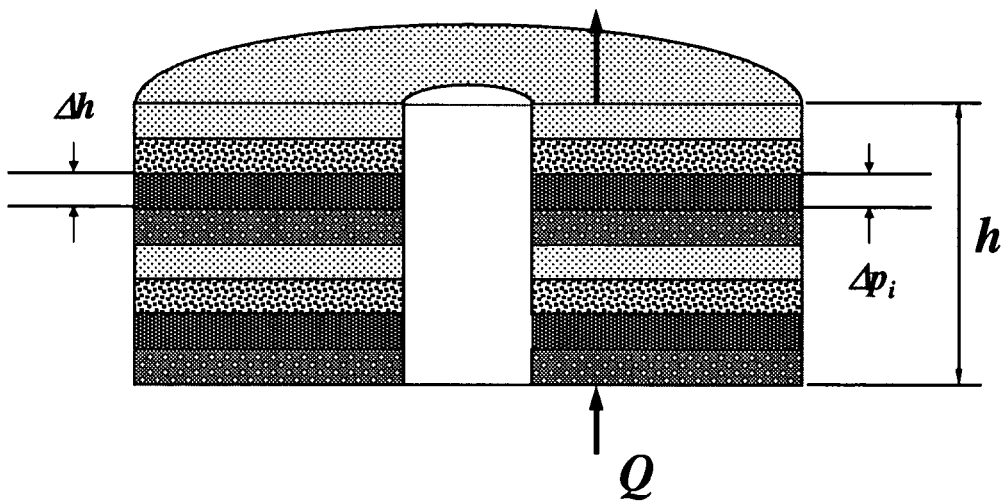

Now consider how fluid would flow vertically through the interval of reservoir 210 as shown in FIG. 4. Let $\Delta P_i$ be the differential pressure across layer i. In this case the linear Darcy equation would apply (i.e., Eq. 2) because fluid flows in a serial path across each layer. Thus, in another aspect of the invention, the individual pressure differential across each layer can be summed to determine the total pressure change across the interval:

$$\Delta P = \frac{h}{k_{ev}} \frac{\mu Q}{A} = \frac{\mu Q}{A} \sum_{i=1}^{n} \frac{\Delta h_i}{k_{vi}} \qquad (8)$$

where A is the constant cross-sectional area of reservoir 210, $\Delta h_i$ is the height of layer i, $k_{vi}$ is the vertical permeability of layer i, and $k_{ev}$ is the interval's equivalent vertical permeability of layer i. Solving for the interval's equivalent vertical permeability $k_{ev}$ yields the following expression.

$$k_{ev} = \frac{h}{\sum_{i=1}^{n} \frac{\Delta h_i}{k_{vi}}} \qquad (9)$$

In a specific embodiment of this invention, vertical permeability values can be obtained for individual spatial units (or layers) using Halliburton's RDT tool. (Details of using RDT tools to estimate permeability is discussed in U.S. patent application Ser. No. 10/254,310, filed on Sep. 25, 2002, to the same assignee as the present application, which is incorporated by reference.) Therefore, the flow interval's equivalent vertical permeability may be estimated based on Eq. 9. In accordance with another embodiment, by making the simplifying assumption that each layer has a uniform thickness and that each layers properties are uniform in all directions (i.e., $k_{hi}=k_{vi}$), Eq. 9 can be simplified as follows.

$$k_{ev} = \frac{h}{\Delta h \sum_{i=1}^{n} \frac{1}{k_{hi}}} = \frac{n}{\sum_{i=1}^{n} \frac{1}{k_{hi}}} \quad (10)$$

In a specific embodiment, the simplifying assumption in Eq. 10 enables the use of horizontal permeability measurements obtained for spatial units in the formation using NMR data to estimate the equivalent vertical permeability of a spatial unit in the formation. Furthermore, if anisotropy information is available for each layer then this can also be included in a more general form of the equation for vertical permeability as follows, where $\lambda_i$ is anisotropy for the i-th layer:

$$k_{ev} = \frac{h}{\sum_{i=1}^{n} \frac{\Delta h_i}{\lambda_i k_{hi}}} \quad (11)$$

Anisotropy data for individual layers can be obtained in accordance with this disclosure by mathematical modeling, prior knowledge, or various types of measurements. In one aspect of the invention, anisotropy values known for a particular formation property may be used in Eq. 11 to provide an anisotropy estimate for another formation property of a spatial unit, if a mathematical or empirical connection between the two can be established. More broadly, in accordance with an aspect of this invention, information from different measurements and relating to different formation properties can be combined in determining estimates for one or more directional formation properties of a spatial unit.

Equations 7 and 10 can also be developed by an electrical analogy. For horizontal flow into the wellbore each layer acts as resistor in parallel circuit where the resistance to flow is $1/\Delta h_i k_{hi}$. For vertical flow each layer acts in series where the resistance to flow in each layer is $\Delta h_i/k_{hi}$.

The most general equation for permeability can be applied to nearly any source of data (i.e., Eq. 6 and 9). For example, if core data exist for a given interval then each core can be used even if it is unequally spaced. This would also apply to wireline tester data where test are taken at unequal depths or even well test data if several well tests were performed in an interval. For wireline log data, like the MRIL permeability curve, the simpler Eqs. 7 and 10 can be used.

After obtaining the directional values (i.e., the horizontal and vertical permeabilities), a variety of anisotropic estimation of the geological formation of interest can be made. In one embodiment, the ratio of the vertical to horizontal equivalent permeabilities is determined by $$\frac{k_{ev}}{k_{eh}} = \lambda_e \quad (12)$$

$$= \frac{h}{\sum_{i=1}^{n} \frac{\Delta h_i}{k_{vi}} \frac{1}{h} \sum_{i=1}^{n} \Delta h_i k_{hi}}$$

$$= \frac{h^2}{\Delta h_i^2 \sum_{i=1}^{n} \frac{1}{k_{vi}} \sum_{i=1}^{n} k_{hi}}$$

$$= \frac{h^2}{\Delta h_i^2 \sum_{i=1}^{n} \frac{1}{k_{vi}} \sum_{i=1}^{n} k_{hi}}$$

In another embodiment, vertical and horizontal permeability values are used to predict the productivity index PI of a well, for example, by the following equation:

$$PI = \frac{a_1 k}{B\mu\left(\ln\frac{r_e}{r_w} - 0.75 + S\right)} \quad (13)$$

where B is a formation volume factor, S is skin, mu is fluid viscosity and k depends on permeability anisotropy. Equation 13 is discussed in detail in Pressure Buildup and Flow Test in Wells, by Mattews, Monograph Series, SPE of AIME, Dallas, Tex. (1967), the contents of which are incorporated herein by reference for additional background.

In another embodiment, the spherical permeability is determined from a single probe formation tester which is the geometric mean of the horizontal and vertical permeabilities.

$$k_s = \sqrt[3]{k_v k_h^2} = \sqrt[3]{k_v \left(\frac{k_v}{\lambda}\right)^2} = k_v \left(\frac{1}{\lambda}\right)^{2/3} \quad (14)$$

From this relationship the horizontal and vertical permeabilities can be related to the spherical permeability as follows:

$$k_v = k_s \lambda^{\frac{2}{3}} \quad (15)$$

$$k_h = \frac{k_s}{\sqrt[3]{\lambda}} \quad (16)$$

Now the upscaled anisotropy can be related to the spherical permeability by the following equation:

$$\lambda_e = \frac{k_{ev}}{k_{eh}} = \frac{h^2}{\sum_{i=1}^{n} \frac{\Delta h_i}{k_{si}\lambda_i^{\frac{2}{3}}} \sum_{i=1}^{n} \frac{\Delta h_i k_{si}}{\sqrt[3]{\lambda_i}}} \quad (17)$$

Assuming each layer has the same anisotropy (i.e., $\lambda_i = \lambda_L$) and the same thickness then the upscaled anisotropy reduces to:

$$\lambda_e = \frac{k_{ev}}{k_{eh}} = \lambda_L \frac{n^2}{\sum_{i=1}^{n} \frac{1}{k_{si}} \sum_{i=1}^{n} k_{si}} \quad (18)$$

When the RDT tool is applied in accordance with a preferred embodiment, and where the probes of the RDT tools are closely spaced, each probe can be assumed to be in contact with 2 layers. In this case the upscaled anisotropy is simplified by assuming a ratio between the two layers permeability (i.e., $a=k_{si+1}/k_{si}$)

$$\lambda_e = \frac{k_{ev}}{k_{eh}} = \lambda_L \frac{4a}{(1+a)^2} \quad (19)$$

It can be shown that the same equation results if a layered sequence is assumed to have the same layers and is infinitely thick.

The parameter "a" can be determined from the drawdown permeability from each probe. The interlayer anisotropy $\lambda_L$ can be determined from the pressure that propagates to the second probe. In any case, Eq. 11 can still be used to determine the extent of anisotropy due to layering by assuming $\lambda_L$ is unity.

In another embodiment, upscaled resistivity estimates are obtained based on the property measurements. Obtaining upscaled resistivity estimates is very important to reserve estimation. Moreover, when it is difficult to directly measure or determine permeability anisotropy, resistivity measurements or resistivity anisotropy may be utilized to predict permeability anisotropy. Details of the relationship between resistivity and permeability anisotropy can be found, for example, in "On the Relationship between Resistivity and Permeability Anisotropy", by Geogi, Bespalov, Tabarovsky, Hughes and Schoen, SPE 77715, 77th Annual Technical Conference of the SPE, San Antonio, Tex., Sept. 29–Oct. 2, 2002, the contents of which are hereby expressly incorporated by reference for additional background.

To obtain upscaled resistivity estimates, recall that Equations 7 and 10 can also be developed by an electrical analogy. For horizontal flow into the wellbore the each layer acts as resistor in parallel circuit where the resistance to flow is $1/\Delta h_i k_{hi}$. For vertical flow the each layer acts in series where the resistance to flow in each layer is $\Delta h_i/k_{hi}$. Derivations for electromagnetic properties identical to the above can be carried out, with pressure drop replaced by voltage, fluid rate replaced by current, and permeability replaced by the reciprocal of resistivity. Thus upscaled $R_v$ and $R_h$ and $R_v/R_h$, can be obtained in analogous fashion. The upscaled equivalent resistivity can be expressed as follows:

$$R_{he} = \frac{1}{h} \sum_{i=1}^{n} \frac{\Delta h_i}{R_{hi}} \quad (20)$$

$$R_{ev} = \frac{h}{\sum_{i=1}^{n} \Delta h_i R_{vi}} \quad (21)$$

where $R_{he}$ is horizontal resistivity, $R_{ev}$ is vertical resistivity, $R_{hi}$ is the horizontal resistivity of the i-th layer and $R_{vi}$ is the vertical resistivity of the i-th layer.

As before by making the simplifying assumption that each layer has a uniform thickness and that each layers properties are uniform in all directions (i.e., $R_{hi}=R_{vi}$), equations 19 and 20 can be simplified as follows.

$$R_{he} = \frac{1}{n} \sum_{i=1}^{n} \frac{1}{R_{hi}} \quad (22)$$

$$R_{ev} = \frac{n}{\sum_{i=1}^{n} R_{hi}} \quad (23)$$

In one embodiment, resistivity anisotropy $\lambda_{erv}$ is defined as follows:

$$\lambda_{erv} = \sqrt{\frac{R_{ev}}{R_{eh}}} \quad (24)$$

The problem of dip angle has been considered in the resistivity logging literature and is related to anisotropy as follows:

$$R_a = \frac{R}{\sqrt{\sin^2(\alpha) + \lambda_r \cos^2(\alpha)}} \quad (25)$$

Where $R_a$ is the apparent resistivity and R is the geometric mean resistivity defined as:

$$R = \sqrt{R_v R_h} \quad (26)$$

Recently introduced logging tools have the capability of determining Rv and Rh.

In another embodiment, upscaled porosity estimates are obtained based on porosity measurements. Obtaining porosity measurements and estimates is important in practice, because for certain geological formations, permeability and porosity are highly correlated. Therefore, when measurements of permeability are difficult to obtain, porosity, besides resistivity, may also be used to predict permeability. Detailed description of the relationship between permeability and porosity in certain geological formations can be found, for example, in "Permeability of shaly sands", by Revil and Cathles III, Water Resources Research, March 1999, vol. 35, No. 3, 651–662; "Mechanisms controlling the permeability of clays", by Mesri and Olsen, Clays Clay Miner., 1971, 19, 151–158; "Permeability-Porosity Relationships in Sedimentary Rocks", by Nelson, Log Analyst, May-June 1994, 38–61; "Permeability Prediction in Poorly Consolidated Siliciclastics Based on Porosity and Clay Volume Logs", by Vemik, Petrophysics, March-April 2000, 138–147; and "Quick-look permeability estimates using sidewall samples and porosity logs", by Van Baaren, 6th Annual European Logging Symposium Transactions, SPWLA, 1979. The contents of the above publications are hereby expressly incorporated by reference for additional background.

To obtain upscaled porosity estimates, consider first 2 layers for simplicity and as shown in FIG. 3, assuming the flow moves serially in the vertical direction with a constant Darcy speed, the pressure measurement is defined as:

$$q = \frac{k_1 k_2 \Delta P}{\mu(k_1 h_2 + k_2 h_1)} \quad (27)$$

where q is the flowrate through layers 1 and 2, $k_1$, $k_2$ are the permeabilities of layer 1 and 2, respectively, $h_1$ and $h_2$ are the height of layer 1 and 2, respectively, and $\Delta P$ is the differential pressure across layer 1 and 2.

The time needed for the fluids to move through layer 1 and 2 is:

$$T_1 = \phi_1 \frac{h_1}{q} \quad (28)$$

$$T_1 = \phi_2 \frac{h_2}{q} \quad (29)$$

The average flow velocity is:

$$q_{avg} = \frac{h_1 + h_2}{T_1 + T_2} = q \frac{h_1 + h_2}{h_1 \phi_1 + h_2 \phi_2} \quad (30)$$

where $\phi_1$, $\phi_2$ are the porosity of layer 1 and 2, respectively.

Therefore the equivalent or effective vertical porosity can be obtained from Eq. 22 for a 2 layer system as follows.

$$\phi_{ev} = \frac{h_1 \phi_1 + h_2 \phi_2}{h_1 + h_2} \quad (31)$$

Figure 6:
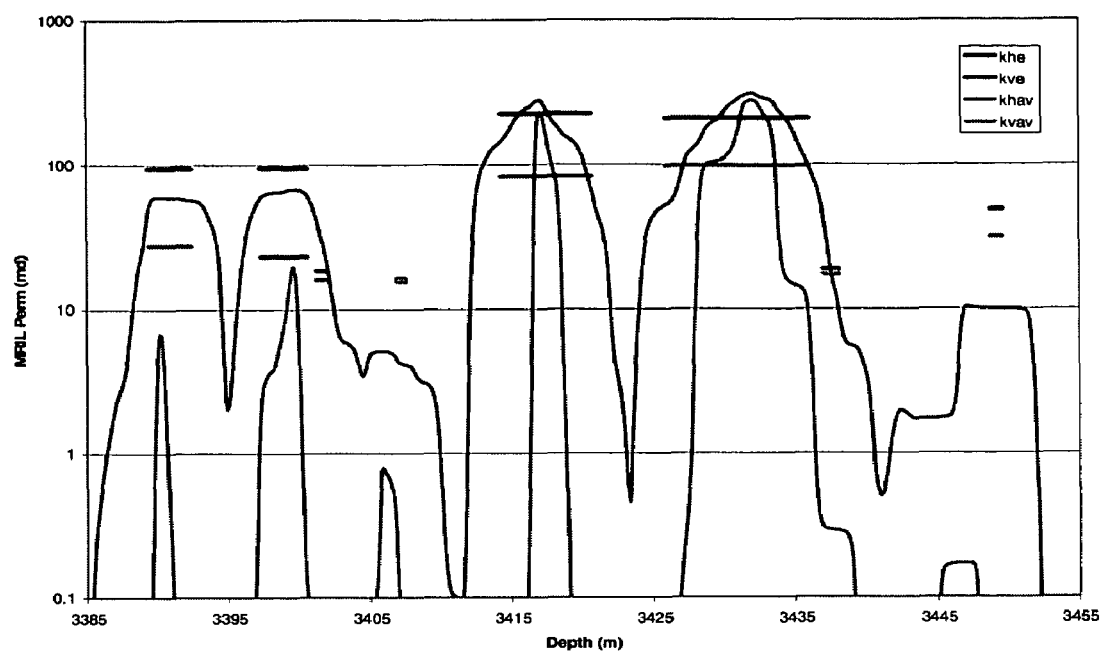
FIG. 6 illustrates a NMR permeability curve showing up-scaled horizontal and vertical permeability with a moving average.

In general, if there are n layers in the flow of FIG. 6 then the following effective vertical porosity $\phi_{ev}$ can be determined:

$$\phi_{ev} = \frac{\sum_{i=1}^{n} h_i \phi_i}{\sum_{i=1}^{n} h_i} \quad (32)$$

Imaging tools are normally associated with resistivity measurements. In this case, small sensors are placed on a pad that measures the local resistivity at the well bore surface. A tool may contain 4 or more pads that can cover most of the borehole wall. By displaying these localized resistivities in two and three dimensional plots, small features of the formation can be observed through the image produced. Acoustic measurements are also used in imaging and the acoustic properties can also be used to map the borehole wall and detect geologic features. More recently, gamma and neutron measurements have been used to produce borehole images and even NMR imaging has been proposed.

In previous geological measurement applications, the properties are determined in one direction only (i.e., depth). The advantage of imaging tools is that they contain rock information in three dimensions, that is, both vertically and azimuthally around the borehole. Therefore, it is possible to interpret this data in more detail than with logs that produce only depth associated information.

Figure 9:
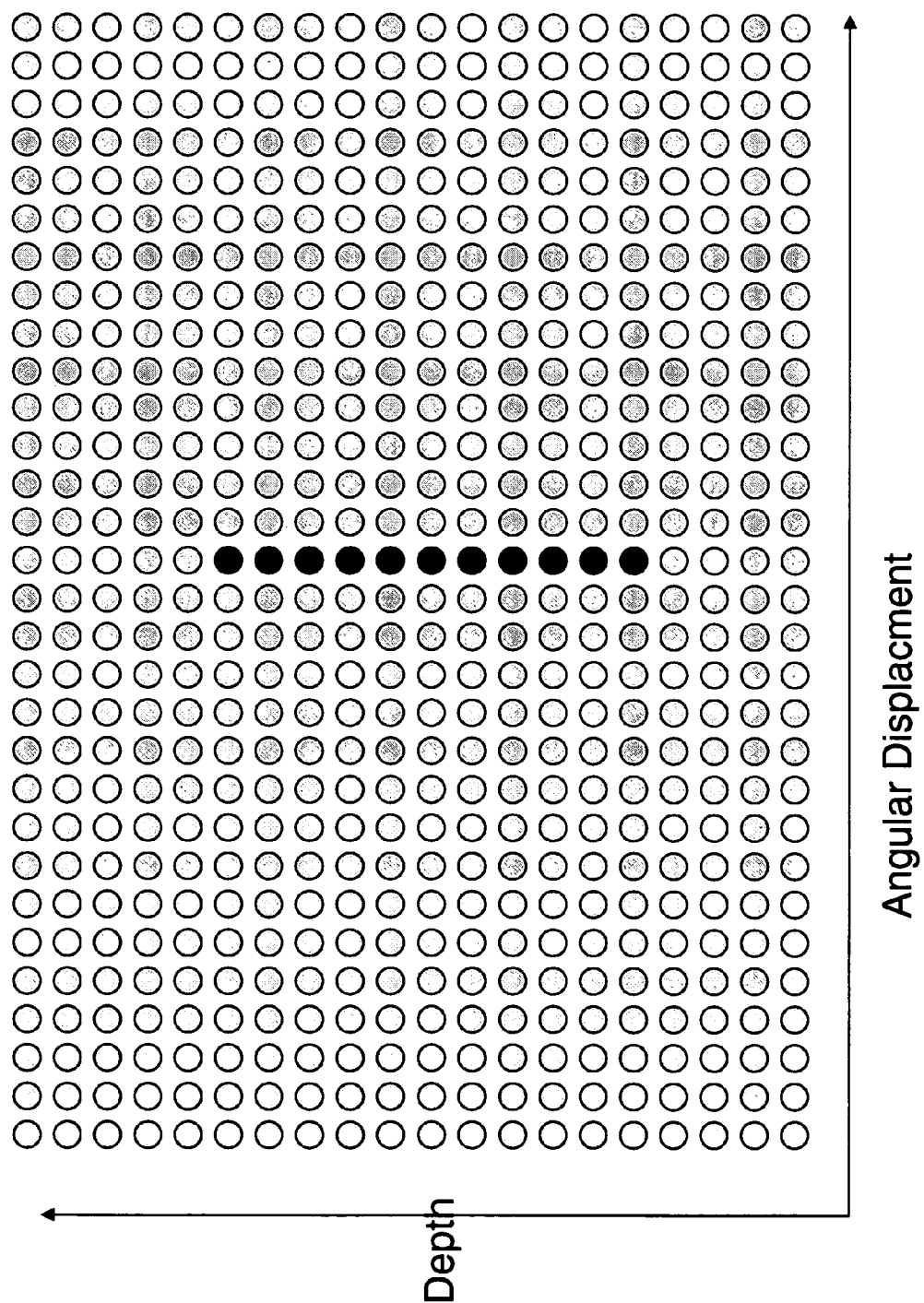
FIG. 9 shows displayed pixels, where the positions of the points are arrayed with depth in the vertical axis and angular displacement in the horizontal axis.
Figure 10:
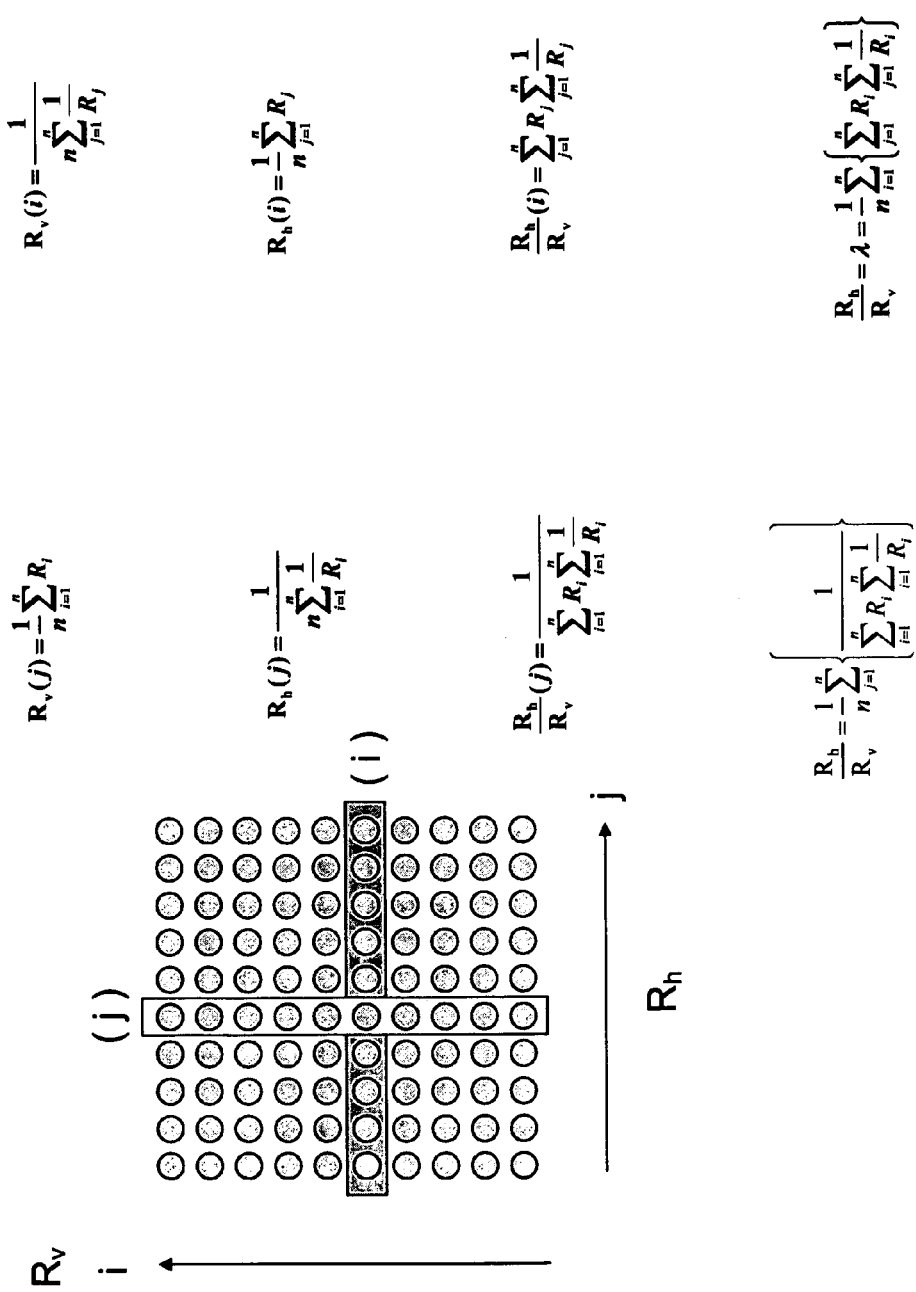
FIG. 10 shows a single valued point derived by resolving a frame of data by summing the upscaled resistivities in both directions.

Consider a resistivity imager that takes an array of measurements around the borehole. This information is composed of an array of measurements much like the pixels in a photograph. These pixels can be displayed as shown in FIG. 9, where the position of the points are arrayed with depth in the vertical axis and angular displacement in the horizontal axis. The highlighted or darker points shown in the center are aligned in the vertical direction and it is possible to upscale these points as shown previously. If these points contain resistivity values then equations 22 and 23 can be applied to determine the upscaled horizontal and vertical resistivity associated with these points. With the additional information available with image data, the points can also be considered as shown in FIG. 10. Here we consider the information contained in a frame of data. The upscaling can be performed in the vertical and horizontal directions. Now, by summing the upscaled resistivities in both directions the entire frame of data is resolved into a single valued point as demonstrated in FIG. 10. By summing the points in the vertical direction (i) for a single borehole position (j) the following values of resistivity and anisotropy are determined.

$$R_v(j) = \frac{1}{n} \sum_{i=1}^{n} R_i \quad (33)$$

$$R_h(j) = \frac{1}{n \sum_{i=1}^{n} \frac{1}{R_i}} \quad (34)$$

$$\lambda(j) = \frac{R_h}{R_v}(j) = \frac{1}{\sum_{i=1}^{n} R_i \sum_{i=1}^{n} \frac{1}{R_i}} \quad (35)$$

Now, by summing each of the vertical rows (j) values an anisotropy can be determined from the entire array.

$$\lambda = \frac{R_h}{R_v} = \frac{1}{k} \sum_{j=1}^{n} \left\{ \frac{1}{\sum_{i=1}^{n} R_i \sum_{i=1}^{n} \frac{1}{R_i}} \right\} \quad (36)$$

This process can be repeated starting with a horizontal position and then summing vertically as follows:

$$R_v(i) = \frac{1}{n \sum_{j=1}^{n} \frac{1}{R_j}} \quad (37)$$

$$R_h(i) = \frac{1}{n} \sum_{j=1}^{n} R_j \quad (38)$$

$$\lambda(i) = \frac{R_h}{R_v}(i) = \sum_{j=1}^{n} R_j \sum_{j=1}^{n} \frac{1}{R_j} \quad (39)$$

-continued $$\lambda = \frac{R_h}{R_v} = \frac{1}{n}\sum_{i=1}^{n}\left\{\sum_{j=1}^{n}R_i\sum_{j=1}^{n}\frac{1}{R_i}\right\} \quad (40)$$

Now that this single frame has been analyzed the process is repeated by shifting the frame both vertically and horizontally until the entire image data is analyzed. If the frames are shifted just one array position, then a new image log can be created for anisotropy. In another technique, the entire array of data over an interval is considered and a anisotropy log much like that shown in FIG. 7 can be produced.

Figure 11:
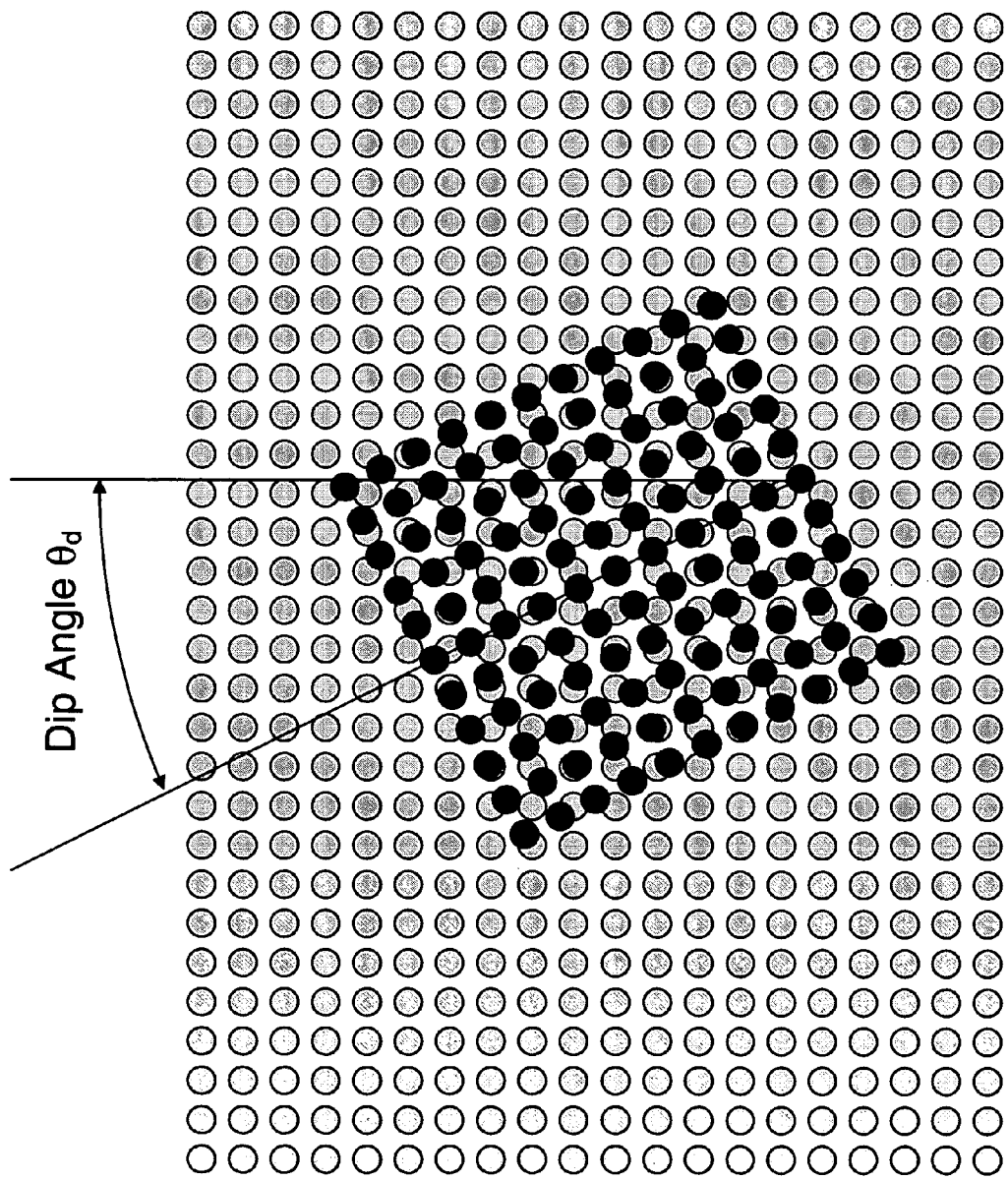
FIG. 11 shows a rotated image frame according to an assumed dip angle $\theta_d$ as shown.

The image analysis shown previously assumes that the anisotropy is aligned vertically. This is rarely the case and the next embodiment considers a dip angle associated with the upscaled properties. This is done by rotating the image frame according to an assumed dip angle $\theta_d$ as shown in FIG. 11. While the points on this frame of data do not lie on top of the measured points, interpolation can be used between the measured data points to determine their resistivity. Then the same process is conducted (Eq. 33 thru 40) on this frame. This value of anisotropy can be compared against the vertical direction. If it produces a lower value of anisotropy then this estimate has improved the measurement. The process is then repeated until a minimum value of anisotropy is determined. The dip angle associated with this minimum value of anisotropy best characterizes this frame of data. As with the previous image processing embodiment, an image log can be produced by shifting the frames or considering a depth interval. Additionally, two upscaled logs can be produced showing anisotropy and the dip angle associated with this anisotropy. Furthermore, by considering the special distribution of the data, it is also possible to develop anisotropy tensors for a depth interval.

While examples of permeability, resistivity and porosity are highlighted here the technique can be applied to other types of data. As long as the physics is honored virtually any rock property, for example speed of sound and other mechanical rock properties could be up-scaled. Image data could also be used for determining anisotropy were the image intensity of each layer is used. Imaging's fine scale measurement would help better define anisotropy where the bedding texture can be lost in may logs. Details of the use of borehole electrical images in estimating the permeability and porosity of geological formations can be found in "Permeability and Porosity Upscaling in the Near-Wellbore Domain: The Contribution of Borehole Electrical Images", by Delhomme, Bedford and Kennedy, 1996 SPE European Petroleum Conference, Milan, Italy Oct. 22–24, 1996, the contents of which are hereby expressly incorporated by reference for additional background.

Figure 5:
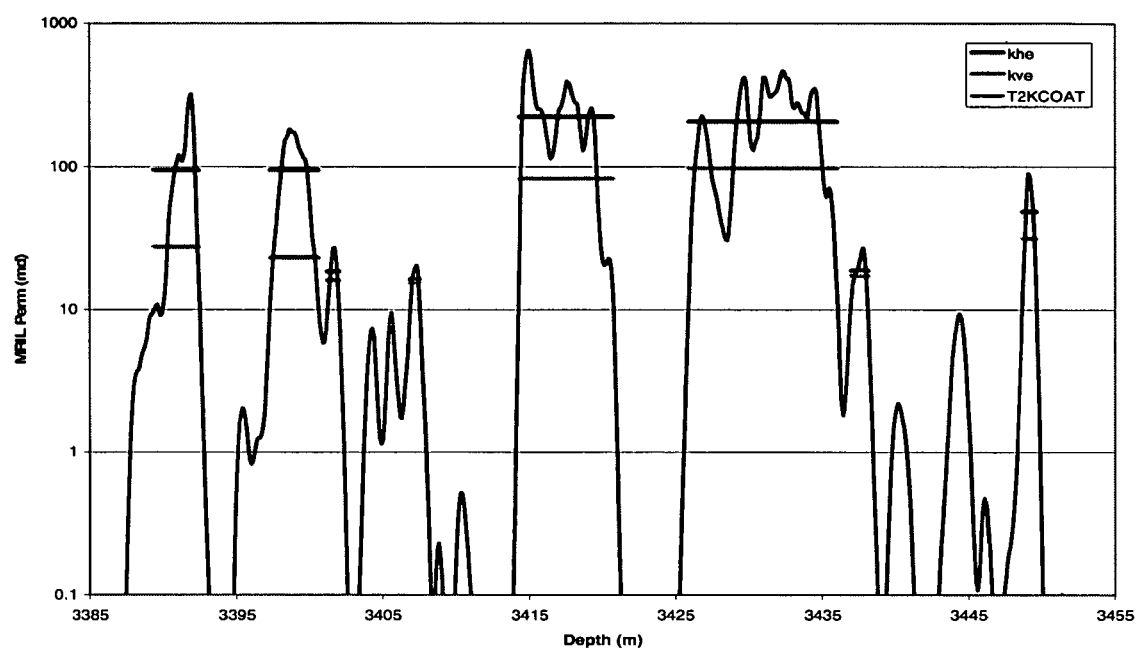
FIG. 5 illustrates a NMR permeability curve showing up-scaled horizontal and vertical permeability in auto selected intervals.
Figure 7:
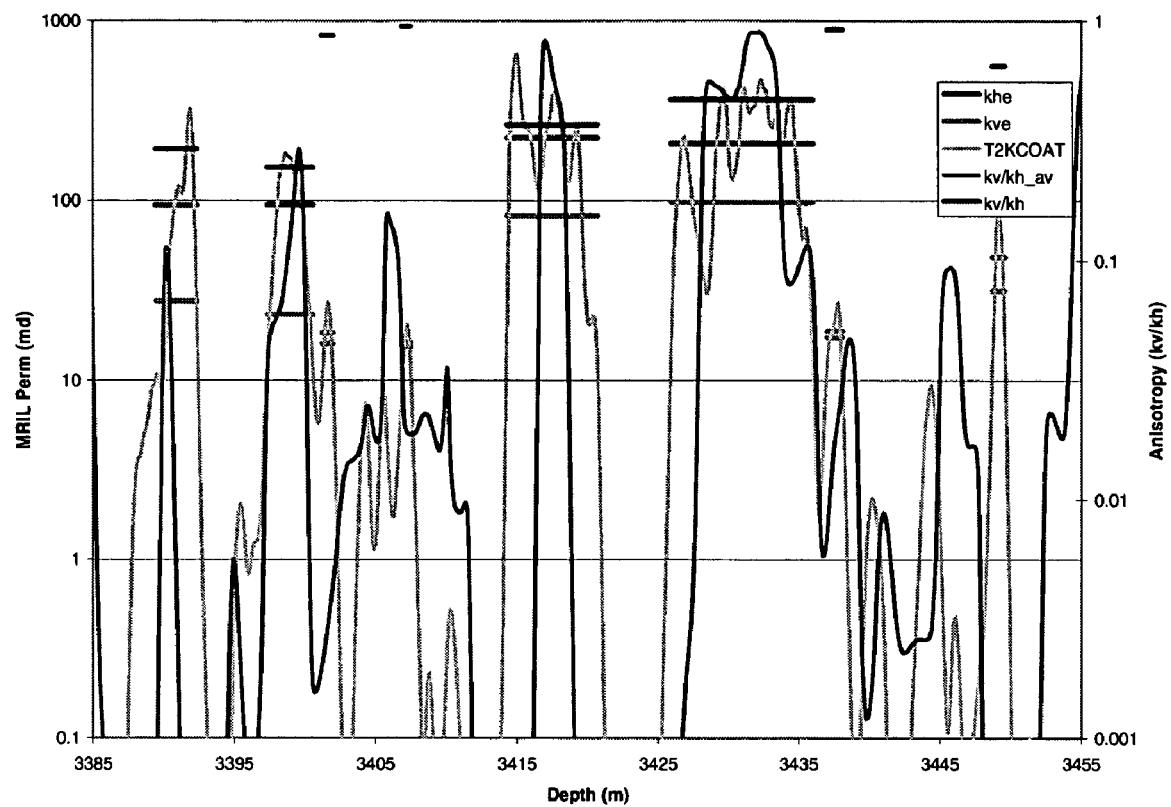
FIG. 7 shows a permeability anisotropy curve derived in accord with the present invention.
Figure 8:
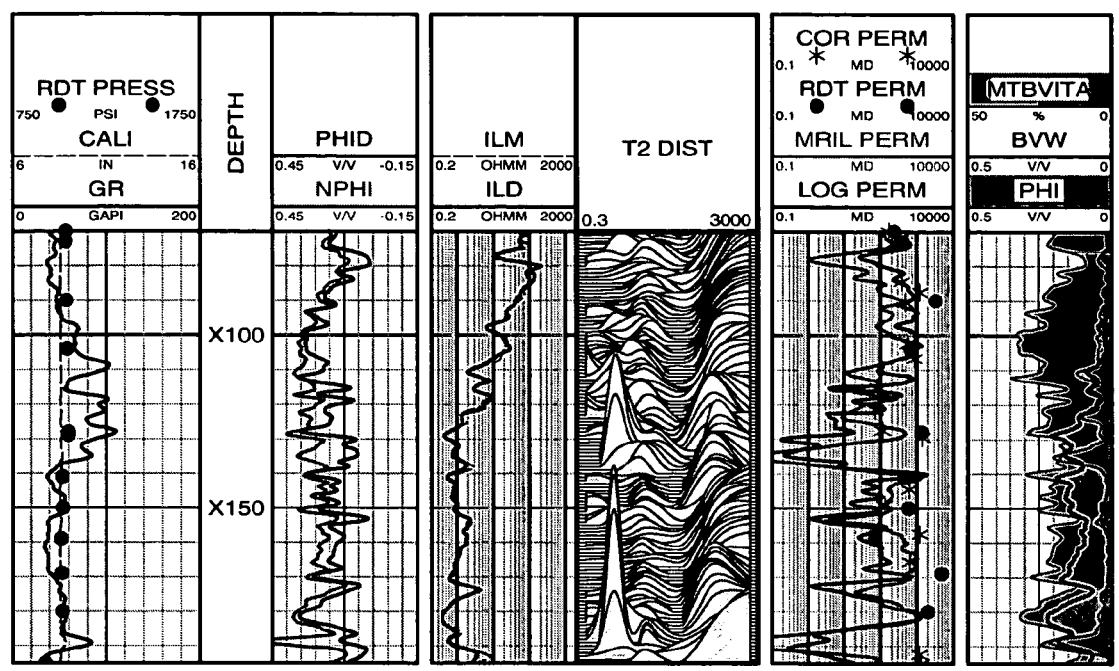
FIG. 8 shows a track of measurements obtained from NMR logs and core or RDT pressure tests, as well as permeability determined from the measurements.

The methods associated with different embodiments described above can be implemented in another aspect of the invention as software programs, taking input from the respective measurement data. These software programs can associate different directional property values with spatial units along the path in the formation based on the measurement data. They can also provide a directional property log for the path, which is a collection of upscaled from the directional property values associated with the spatial units. The log may be expressed in a graphical form. Such graphs may present a log upscaled in auto selected intervals and upscaled in moving-average intervals. Also, in case of a permeability log, equivalent horizontal permeability $k_{he}$ in a segment, equivalent vertical permeability $k_{ev}$ in a segment, or a combination thereof may be shown a grpah. These software programs can be integrated into existing tester tools, such as Halliburton's RDT, in the processing of logged data or other measurement data. The above methods can be very efficient when incorporated with logging tools, such as the MRIL family NMR tools. For example, if a minimum value of permeability is chosen then intervals can be selected immediately. Permeability upscaling can be determined in real time based on, for example, equations 1–18 and a permeability log can be maintained in the LWD operation. FIG. 5 shows a permeability curve obtained in a MRIL log. A moving average can also be used to smooth the MRIL curve as shown in FIG. 6. The moving average is less sensitive to layering effects on vertical permeability due to the low permeability values between the beds. FIG. 7 shows a permeability anisotropy curve, illustrating the ratios of vertical permeability or horizontal permeability in each flow interval. Finally, FIG. 8 shows a track of measurements obtained from MRIL logs and core or pressure tests obtained using Halliburton's RDT, as well as permeability determined from the measurements.

While the above invention has been described with reference to certain preferred embodiments, the scope of the present invention is not limited to these embodiments. One skilled in the art may find variations of these embodiments which, nevertheless, fall within the spirit of the present invention, whose scope is defined by the claims set forth below. For additional information the interested reader is directed to the disclosure in the attached appendices, including SPE Paper Nos. 77345 and 77715 (both 2002) and a paper on thinly laminated reservoir evaluation, presented at the 43 annual SPWLA Symposium, 2002, which are incorporated herein by reference for additional background.

What is claimed is:

1. A method for investigating a geologic formation, comprising the steps of:
   measuring a property of the formation in one or more directions along a path in the formation;
   associating directional property value(s) with a plurality of spatial units along the path in the formation based on the property measurements; and
   providing a directional property log for the path in the formation, the log being upscaled from the directional property values associated with the plurality of spatial units.

2. The method of claim 1, wherein the step of measuring comprises obtaining at least one NMR log along the path in the formation.

3. The method of claim 1, wherein the property of the formation being measured is one or more of: permeability, resistivity, porosity, diffusivity, or viscosity.

4. The method of claim 1, wherein upscaling the obtained directional property values comprises averaging property measurements over at least one of the plurality of spatial units along the path in the formation.

5. The method of claim 4, wherein the property of the formation being measured is permeability, and equivalent horizontal permeability for a segment of the provided directional property log is computed using as the expression:

$$k_{he} = \frac{1}{h}\sum_{i=1}^{n}\Delta h_i k_{hi}$$

where $k_{he}$ is the equivalent horizontal permeability in the segment, $k_{hi}$ is the horizontal permeability of the i-th layer of the geological formation within the segment, n is the number of layers in the segment, h is the length of the segment and $\Delta h_i$ is the length of the i-th layer.

6. The method of claim 4, wherein the property of the formation being measured is permeability, and equivalent vertical permeability for a segment of the provided directional property log is computed using as the expression:

$$k_{ev} = \frac{h}{\sum_{i=1}^{n} \frac{\Delta h_i}{k_{vi}}}$$

where $k_{ev}$ is the equivalent vertical permeability in the segment, $k_{vi}$ is the vertical permeability of the i-th layer of the geological formation within the segment, n is the number of layers in the segment, h is the length of the segment and $\Delta h_i$ is the length of the i-th layer.

7. The method of claim 4, wherein the property of the formation being measured is permeability and the step of providing a directional property log comprises estimating the ratio of vertical to horizontal equivalent permeabilities over the at least one of the plurality of spatial units.

8. The method of claim 7, wherein the ratio of the vertical to horizontal equivalent permeabilities for a segment of the provided directional property log is estimated by:

$$\frac{k_{ev}}{k_{eh}} = \frac{h^2}{\Delta h^2 \sum_{i=1}^{n} \frac{1}{k_{vi}} \sum_{i=1}^{n} k_{hi}}$$

where $k_{ev}$ is the equivalent vertical permeability in the segment, $k_{he}$ is the equivalent horizontal permeability in the segment, $k_{vi}$ and $k_{hi}$ are the vertical and horizontal permeabilities of the i-th layer of the geological formation within the segment, respectively, n is the number of layers in the segment, $\Delta h$ is the length of the segment and $\Delta h$ is the height of the each layer.

9. The method of claim 6, wherein assuming that each layer has uniform thickness and that layers properties are uniform in all directions, the equivalent vertical permeability can be determined as:

$$k_{ev} = \frac{h}{\Delta h \sum_{i=1}^{n} \frac{1}{k_{hi}}} = \frac{n}{\sum_{i=1}^{n} \frac{1}{k_{hi}}}$$

where $k_{hi}$ is the horizontal permeability of the i-th layer of the geological formation within the segment, and n is the number of segments in the formation.

10. The method of claim 9, wherein the $k_{hi}$ horizontal permeabilities are determined using an NMR measurement log.

11. The method of claim 1, wherein the property of the formation being measured is permeability and a relationship between anisotropy and spherical permeability is determined by:

$$k_s = \sqrt[3]{k_v k_h^2} = \sqrt[3]{k_v \left(\frac{k_v}{\lambda}\right)^2} = k_v \left(\frac{1}{\lambda}\right)^{\frac{2}{3}}$$

where $k_s$ is the spherical permeability in a segment; $k_v$ and $k_h$ are the vertical and horizontal permeabilities, respectively; and $\lambda$ is the upscaled anisotropy.

12. The method of claim 11, wherein the upscaled anisotropy $\lambda_e$ estimate in a segment is determined by $$\lambda_e = \frac{h^2}{\sum_{i=1}^{n} \frac{\Delta h_i}{k_{si} \lambda_i^{\frac{2}{3}}} \sum_{i=1}^{n} \frac{\Delta h_i k_{si}}{\sqrt[3]{\lambda_i}}}$$

where k is the spherical permeability of the i-th layer in the geological formation, n is the number of layers in the segment, h is the length of the segment and $\Delta h_i$ is the height of the i-th layer.

13. The method of claim 1, wherein assuming each layer in a segment of the geologic formation along the path has the same anisotropy and same thickness, the upscaled anisotropy estimate $\lambda_e$ of the segment is determined by $$\lambda_e = \lambda_L \frac{n^2}{\sum_{i=1}^{n} \frac{1}{k_{si}} \sum_{i=1}^{n} k_{si}}$$

where $k_{si}$ is the spherical permeability of the i-th layer of the geological formation, $\lambda_L$ is the permeability of each layer in the geological formation; n is the number of layers in the segment.

14. The method of claim 13, wherein the anisotropy estimate is provided by $$\lambda_e = \lambda_L \frac{4a}{(1+a)^2}$$

where $\alpha$ is a ratio between the permeability of two layers in the geological formation, $\lambda_L$ is the anisotropy of a layer in the geological formation and $\lambda_e$ is the upscaled anisotropy estimate.

15. The method of claim 1, further comprising the step of providing the directional property log for the path in the formation in a human-recognizable format.

16. The method of claim 15, wherein the directional property log is expressed in the form of a graph.

17. The method of claim 15, wherein the directional property log is expressed in the form of a graph upscaled in auto selected intervals.

18. The method of claim 15, wherein the directional property log is expressed in the form of a graph upscaled in moving-average intervals.

19. The method of claim 15, wherein the property of the formation being measured is permeability, and directional property log is expressed in the form illustrating one or more of: equivalent horizontal permeability $k_{he}$ in segment, equivalent vertical permeability $k_{ev}$ in a segment, or a combination thereof.

20. The method of claim 19, wherein the directional property log is expressed in the form of a graph up scaled in one of: auto selected intervals, and moving-average intervals.

21. The method of claim 1, wherein the path in the formation comprises a linear path.

22. The method of claim 21, wherein the linear path is vertical.

23. The method of claim 21, wherein the linear path is angled.

24. The method of claim 1, wherein said one or more measurement directions comprise a horizontal measurement direction.

25. The method of claim 1 further comprising the steps of:
obtaining directional property values associated with a first set of formation properties; and
generating directional property values for a second set of formation properties based on the obtained directional property values for the first set of formation property.

26. The method of claim 25, wherein the first formation property comprises resistivity.

27. The method of claim 25, wherein the second set of properties comprises permeability.

28. A system for estimating properties of a geologic formation comprising one or more software programs adapted to execute the method of claim 1.

29. The method of claim 4, wherein the property of the formation being measured is resistivity, and equivalent horizontal resistivity for a segment of the provided directional property log is computed using as the expression:

$$R_{he} = \left\{ \frac{1}{h} \sum_{i=1}^{n} \frac{\Delta h_i}{R_{hi}} \right\}^{-1}$$

where $R_{he}$ is the equivalent horizontal resistivity in the segment, $R_{hi}$ is the horizontal resistivity of the i-th layer of the geological formation within the segment, n is the number of layers in the segment, h is the length of the segment and $\Delta h_i$ is the length of the i-th layer.

30. The method of claim 4, wherein the property of the formation being measured is resistivity, and equivalent vertical resistivity for a segment of the provided directional property log is computed using as the expression:

$$R_{ev} = \left\{ \frac{h}{\sum_{i=1}^{n} \Delta h_i R_{vi}} \right\}^{-1}$$

where $R_{ev}$ is the equivalent vertical resistivity in the segment, $R_{vi}$ is the horizontal resistivity of the i-th layer of the geological formation within the segment, n is the number of layers in the segment, h is the length of the segment and $\Delta h_i$ is the length of the i-th layer.

31. The method of claim 29, wherein assuming that each layer has uniform thickness and that layers properties are uniform in all directions, the equivalent vertical resistivity can be determined as:

$$R_{he} = \left\{ \frac{1}{n} \sum_{i=1}^{n} \frac{1}{R_{hi}} \right\}^{-1}$$

where $R_{hi}$ is the horizontal resistivity of the i-th layer of the geological formation within the segment, and n is the number of segments in the formation.

32. The method of claim 30, wherein assuming that each layer has uniform thickness and that layers properties are uniform in all directions, the equivalent vertical resistivity can be determined as:

$$R_{ev} = \left\{ \frac{n}{\sum_{i=1}^{n} R_{hi}} \right\}^{-1}$$

where $R_{hi}$ is the horizontal resistivity of the i-th layer of the geological formation within the segment, and n is the number of segments in the formation.

33. The method of claim 1, wherein the property of the formation being measured is resistivity and a relationship between anisotropy $\lambda_{erv}$ and vertical resistivity $R_{ev}$ and horizontal resistivity $R_{he}$ is determined by:

$$\lambda_{erv} = \sqrt{\frac{R_{ev}}{R_{eh}}}$$

34. The method of claim 4, wherein the property of the formation being measured is porosity, and equivalent vertical porosity for a segment of the provided directional property log is computed using as the expression:

$$\phi_{ev} = \frac{\sum_{i=1}^{n} h_i \phi_i}{\sum_{i=1}^{n} h_i}$$

where $\phi_{ev}$ is the equivalent vertical porosity in the segment, $\phi_i$ is the vertical porosity of the i-th layer of the geological formation within the segment, n is the number of layers in the segment and $h_i$ is the length of the i-th layer.

35. The method of claim 1, further comprising predicting the productivity of the geological formation based on the upscaled directional values.

36. A method for estimating directional permeability along a path in a geologic formation, comprising the steps of:
measuring permeability values in one or more directions along the path in the formation;
associating directional permeability value(s) with a plurality of spatial units along the path in the formation based on the permeability measurements; and
providing a directional permeability log for the path in the formation, the log being upscaled from the measured permeability values associated with the plurality of spatial units.

37. A system for investigating a geologic formation, comprising:

means for measuring a property of the formation in one or more directions along a path in the formation;

means for associating directional property value(s) with a plurality of spatial units along the path in the formation based on the property measurements; and means for providing a directional property log for the path in the formation, the log being upscaled from the directional property values associated with the plurality of spatial units.

38. The system of claim 37, wherein means for measuring comprises a NMR logging tool.

39. The system of claim 37, wherein said means for measuring comprises a RDT formation tester tool.

40. The system of claim 37, wherein the property of the formation being measured is one or more of: permeability, resistivity, porosity, diffusivity, or viscosity.

41. The system of claim 37, wherein the means for providing the directional property log further comprises means for averaging property measurements over at least one of the plurality of spatial units along the path in the formation.

42. A method for imaging a geologic formation, comprising the steps of:

(a) providing a two- or more dimensional data array corresponding to at least one property value of the formation at a given location;

(b) computing one or more upscaled directional property values at the given location based on a subset of the data array;

(c) repeating steps (a) and (b) over a set of locations in the formation; and (d) generating an image corresponding to the computed directional property values at the locations in step (c).

43. The method of claim 42, wherein the property value is resistivity.

44. The method of claim 42 further comprising the step of displaying the generated image to a human observer.

45. The method of claim 42 further comprising the step of associating a bulk property direction associated with the computed at least one property value of the formation based on the set of locations in step (c).

46. The method of claim 42, wherein the bulk property direction provides the anisotropy of the formation over the set of locations in step (c).

* * * * *